United States Patent [19]

Seamone et al.

[11] 4,067,070
[45] Jan. 10, 1978

[54] PROSTHETIC JOINT LOCK AND CABLE MECHANISM

[75] Inventors: Woodrow Seamone; John H. Loveless, both of Silver Spring, Md.

[73] Assignee: The United States of America as represented by the Administrator of Veterans' Affairs, Washington, D.C.

[21] Appl. No.: 738,580

[22] Filed: Nov. 3, 1976

[51] Int. Cl.² .......................... A61F 1/00; A61F 1/06
[52] U.S. Cl. ............................................. 3/1.1; 3/12.3
[58] Field of Search ....................... 3/1.1, 1.2, 12–12.8

[56] References Cited

U.S. PATENT DOCUMENTS

| 2,535,489 | 12/1950 | Edwards | 3/1.1 |
| 3,735,425 | 5/1973 | Hoshall et al. | 3/1.1 |
| 3,866,246 | 2/1975 | Seamone et al. | 3/1.1 |

OTHER PUBLICATIONS

"Displacement Sensors and their Application to Control of Synthetically Powered Prostheses and Orthoses" by C. H. Hoshall, Bulletin of Prosthetics Research, BPR 10-20, Fall 1973, pp. 4–28.

Primary Examiner—Ronald L. Frinks
Attorney, Agent, or Firm—Browdy and Neimark

[57] ABSTRACT

A joint lock and cable arrangement for an externally powered prosthesis, the arrangement allowing shoulder and/or elbow joint movement of a prosthesis through the use of a single driving motor. The joint lock system includes a release solenoid and an electronic circuit which couples the solenoid and the driving motor, the release solenoid being activated to cause locking at a timed period after the motor is energized, so as to permit the desired operation of the associated joint for such timed period. The arrangement enables the use of a single motor to drive the shoulder joint and elbow joint of a prosthesis, and provides operation of a terminal device when both joints are in locked condition.

12 Claims, 6 Drawing Figures

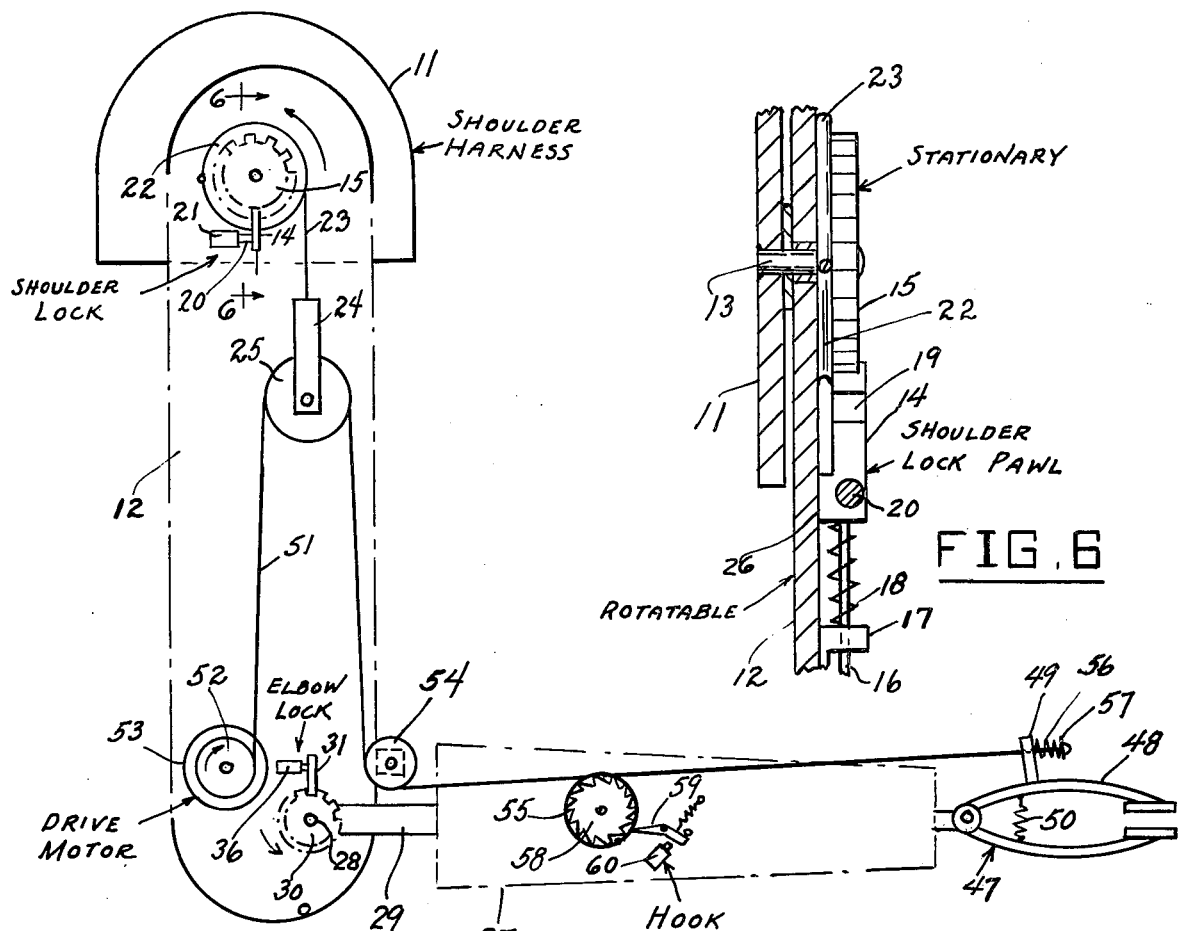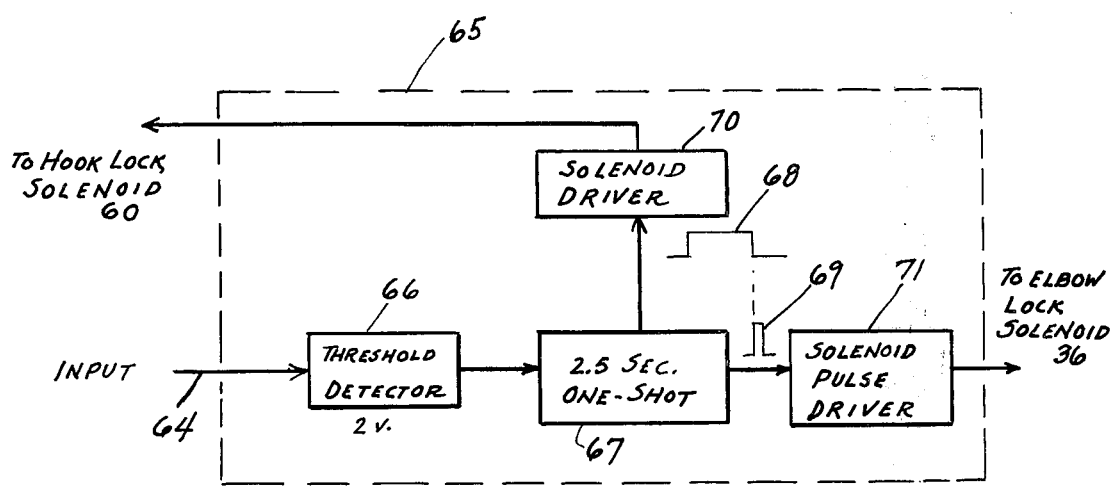

PROSTHETIC JOINT LOCK AND CABLE MECHANISM

FIELD OF THE INVENTION

This invention relates to artificial body members, and more particularly to externally powered prosthesis assemblies having lockable pivoted joints.

BACKGROUND OF THE INVENTION

Various upper limb and other prosthesis systems have been designed, employing myoelectrically controlled and similarly controlled power units. The existing systems have been designed for movement of a specific joint of a prosthesis. Certain types of power units have been developed exclusively for elbow motion, whereas others have been developed exclusively for wrist motion and/or terminal device function. Conventional prosthesis systems must be extensively modified to be compatible with these power units. The appliance is therefore usually created and delivered as a complete unit. Only a limited number of styles and sizes of terminal devices or other conventional components are compatible with many of these currently available artificial limbs. Also, due to their complexity, specifically trained personnel are required for their fabrication, servicing and maintenance. In addition, their cost is high and their availability for general use is limited.

Therefore, there is a substantial need for a simplified externally powered prosthetic system which can be controlled by an EMG, or similar, signal to operate in a proportional mode to control either a hook/hand grasping assembly (terminal device) or an elbow flexion assembly using conventional terminal devices or other components which might be used as part of the total prosthesis.

More specifically, there is a substantial need for a simplified artificial arm structure including a pivoted upper arm element, a forearm element pivoted to the upper arm element to define an elbow joint, and a terminal device, such as a grasping hook assembly, carried by said forearm element, with driving means, such as a motor, to operate the elements, and suitable easily controlled means to selectively lock the various joints at times, whereby the user can perform a wide range of functions closely simulating those available with a normal arm.

SUMMARY OF THE INVENTION

Accordingly, a main object of the invention is to provide for an improved prosthesis assembly.

Another object is to overcome deficiencies in the prior art such as indicated above.

Yet another object is to provide a prosthesis which utilizes many standard, available prosthetic components, which provides a powered elbow and/or powered terminal device, which employs a single motor controllable from a single EMG, or equivalent, transducer site, which provides proportional control, which is easy for an amputee to learn to use, which is reliable and versatile, and which utilizes a power source and powered components which may be conveniently located either on the prosthesis or worn on the user's belt, in accordance with the individual needs of the user.

A further object of the invention is to provide an improved prosthesis assembly employing a single motor unit mounted adjacent the elbow portion of the assembly and employing a cable system having a configuration allowing active shoulder flexion as well as elbow flexion and hook control, the assembly including means for at times locking the pivoted joints and for controlling the timing of the release thereof, the parts being relatively light in weight and being durable in construction, and the assembly providing a substantial extension of the range of movement of its terminal device, as compared with previously devised prosthetic systems of the same general type.

A still further object of the invention is to provide an improved electrically powered prosthesis assembly comprising an artificial arm having a hook-type terminal structure and being provided with controllable locking means for its shoulder and elbow joints, the assembly including a drive motor and a cable system with means for selectively rotating the upper arm and forearm portions of the prosthesis, in accordance with their locked or unlocked conditions and including in its cable arrangement means for automatically operating the hook-like terminal structure responsive to the locked condition of the joints, the prosthesis assembly being relatively simple in construction, being light in weight, being reliable in operation, and being very economical in its consumption of electrical power.

BRIEF DESCRIPTION OF THE DRAWINGS

Further objects and advantages of the invention will become apparent from the following description of embodiments, and from the accompanying drawing thereof, wherein:

FIG. 1 is a diagrammatic view of an improved prosthetic assembly according to the present invention, embodied in an artificial arm.

FIG. 5 is a block diagram of the locking timer circuit, forming part of the circuit system shown in FIG. 2.

FIG. 6 is a vertical cross-sectional view taken substantially on the line 6—6 of FIG. 1 and showing parts associated with a shoulder locking mechanism which may form part of a prosthetic assembly according to the present invention.

DESCRIPTION OF A PREFERRED EMBODIMENT

Figure 2:
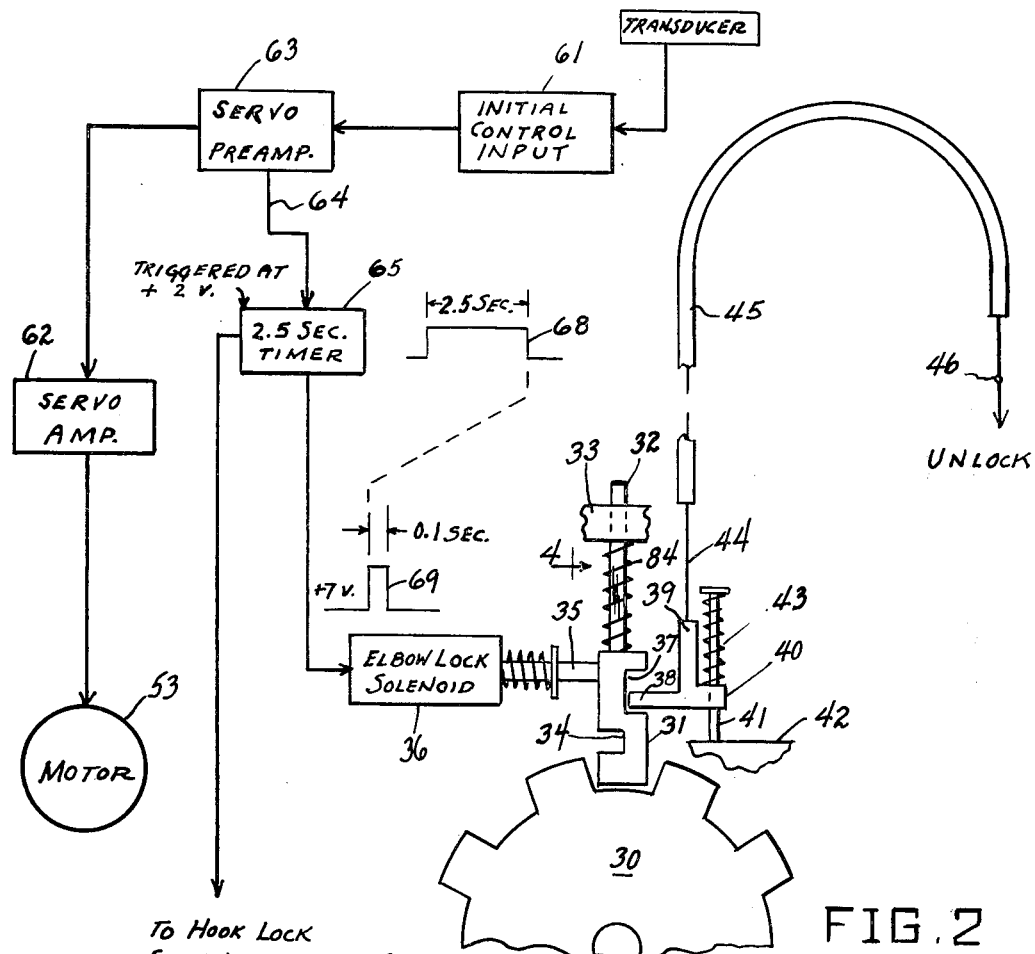
FIG. 2 is a block diagram of the electrical circuit employed in the assembly of FIG. 1 and diagrammatically showing part of the elbow locking mechanism and elements associated therewith, the mechanism being shown in locking position.

Referring to the drawings, and more particularly to FIG. 1, 11 designates a conventional shoulder cap shaped to fit over an amputee's shoulder, said cap being provided with suitable fastening braces or straps, not shown, connected to other supports suitably secured on the wearer's body.

Diagrammatically illustrated at 12 is an upper arm structure, which may comprise a tubular casing of metal or other light and strong suitable material, pivotally connected at its top end to the shoulder cap 11. For example, the top inside wall portion of the upper arm member 12 may be rotatably mounted on a pivot pin 13 rigidly secured to the shoulder cap 11, as shown in FIG. 6.

Upper arm member 12 may be releasably locked against rotation relative to shoulder cap 11 by means of a spring-biased shoulder lock pawl member 14 which lockingly engages the periphery of a toothed locking wheel 15 rigidly secured on pivot pin 13. In the typical structure shown in FIG. 6, the pawl member 14 has a flat surface portion 26 which slidably engages against the inside wall of member 12 and has a depending stem portion 16 slidably engaged through a bearing bracket 17 secured to said inside wall of member 12. A biasing spring 18 surrounds stem 16 and bears between bracket 17 and pawl member 14, urging the pawl member 14 into engagement with toothed wheel 15. Member 14 has a transverse retention recess 19 in which the spring-biased plunger 20 of a holding solenoid, mounted on member 12, is at times receivable, as will be presently explained, to maintain the shoulder joint unlocked. Solenoid 21 is mounted on the inside wall of upper arm member 12 in a position such that when the plunger 20 engages in recess 19 it will latch the pawl member 14 disengaged from the toothed wheel 15. A release cable, not shown, operable by the user, may be connected to stem 16 to enable the user to retract pawl member 14 to its latched lowered position. As will be presently explained, the energization of solenoid 21 may be suitably timed to release the pawl member 14 after upper arm member 12 has been swung to a desired rotated position.

Stationary toothed wheel 15 has an integral peripherally grooved flange 22. A cable element 23 is supported on and has one end secured to the periphery of flange 22. The other end of cable 23 is supportingly connected to a pulley bracket 24 in which a pulley 25 is rotatably supported.

As will be apparent from FIG. 1, tension developed in cable 23 will generate a torque acting on upper arm member 12 tending to rotate it in a counterclockwise direction, as viewed in FIG. 1, namely, in a direction to cause said upper arm member to be lifted when shoulder lock pawl 14 is disengaged from toothed wheel 15.

Figure 3:
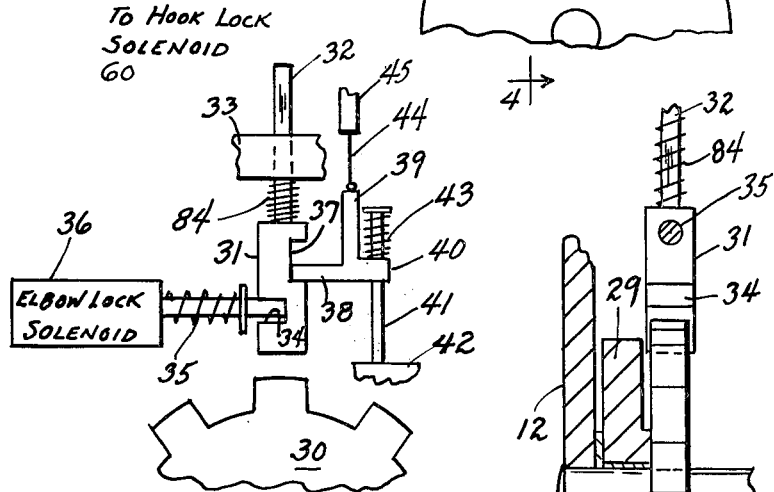
FIG. 3 is a diagrammatic view of the elbow locking mechanism of FIG. 2, shown in elbow-releasing position.
Figure 4:
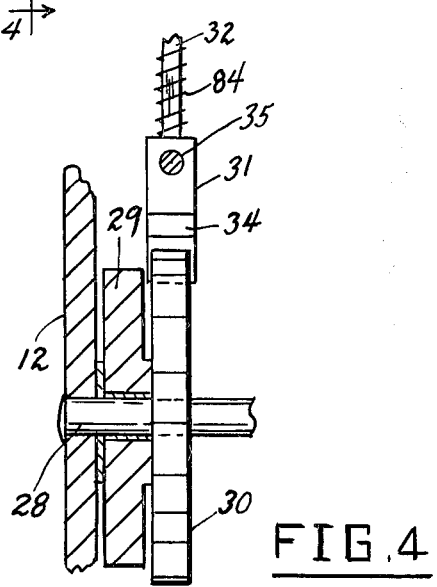
FIG. 4 is a vertical cross-sectional view taken substantially on the line 4—4 of FIG. 2.

The forearm portion of the prosthesis, shown schematically at 27, is pivotally attached to the lower end of the upper arm member 12 by a pivot shaft 28. For example, the shaft 28 may be rigidly secured to member 12 and forearm member 27 may be provided with an extension bar 29 rotatably engaged on shaft 28, as shown in FIG. 4. Extension bar 29 is provided with a rigidly-connected toothed wheel 30 concentric with shaft 28 lockingly engageable by a radially disposed pawl member 31 suitably slidably supported in upper arm member 12. For example, as shown in FIGS. 2, 3 and 4, pawl member 31 may have a squared extension rod 32 slidably and non-rotatably engaged through a bracket 33 mounted in member 12, with a biasing spring 84 surrounding rod 32 and bearing between bracket 33 and pawl member 31, biasing member 31 toward toothed wheel 30. Pawl member 31 has a transverse locking recess 34 in which the end of the spring-biased plunger 35 of an elbow locking solenoid 36 is receivable when the pawl member 31 is in an unlocking position, as shown in FIG. 3. Solenoid 36 is suitably mounted in member 12 in a position such that plunger 35 can enter recess 34 when pawl member 31 is retracted from toothed wheel 30. Pawl member 31 is formed with another, vertically elongated, recess or notch 37 on the side thereof opposite recess 34 in which the bottom lug 38 of a retractor 39 is received. Retractor 39 has an arm 40 slidably but non-rotatably engaged on a headed guide rod 41 carried by a bracket 42 suitably mounted in upper arm member 12, arranged to guide retractor 39 for movement parallel to pawl member 31. A biasing spring 43 surrounds the upper portion of guide rod 41 and bears between the head thereof and arm 40, biasing pawl member 31 downwardly.

Connected to the top end of retractor 39 is an unlocking cable 44 guided in a conventional manner in a sheath 45 and arranged to be actuated by a predetermined muscular command movement of the user. Thus, the end of the cable is connected at 46 to respond to such a command movement to develop a pull on the cable to move the retractor 39 upwardly so as to cause lug 38 to engage the top end of recess 37 and to thereby elevate pawl member 31 sufficiently to allow plunger 35 to latch it in unlocking position, shown in FIG. 3. Plunger 35 releases pawl member 31 responsive to the energization of solenoid 36, in a manner presently to be explained, to lock the elbow joint, as shown in FIG. 2.

A conventional terminal device, such as a hook assembly 47, is provided on the forward end of the forearm portion 27, said assembly 47 having the upper pivoted element 48 provided with the operating lug 49. Hook assembly 47 is biased toward closing or gripping condition in a conventional manner by relatively strong spring means 50.

An operating cable 51 extends from a cable reel 52 secured on the shaft of a drive motor 53 mounted in upper arm member 12 adjacent the elbow joint. Cable 51 extends over pulley 25 and beneath an idler pulley 54 journalled on the upper arm member 12 forwardly adjacent the elbow joint, as shown in FIG. 1. Said cable 51 extends a full turn around and is secured to an idler pulley 55 journalled in forearm member 27, and is resiliently connected to hook-operating lug 49. Thus, cable 51 extends through the lug 49 and a compliance spring 56 and is anchored to an end retaining washer 57 in the manner diagrammatically illustrated in FIG. 1.

Idler pulley 55 is provided with a ratchet wheel 58 lockingly engageable by a pivoted pawl 59 provided on forearm member 27 and controlled by a hook lock solenoid 60 mounted on member 27, for at times locking the cable 51 relative to the hook-opening lug 49, as will be presently described.

Compliance spring 56 is relatively stiff, so that the tension developed in cable 51 by the operation of motor 53 will not be sufficient to open the hook assembly unless both the shoulder and elbow joints are locked.

Referring to FIG. 2, it will be seen that the motor 53 is energized responsive to the generation of an appropriate signal in an "initial control input" stage, designated at 61. This signal may be derived in any suitable manner as a response to specific muscular command movement of the user, for example, as an EMG signal obtained from a conventional skin muscle sensor. Alternatively, a magnetic motion detector may be used to provide a proportional signal by suitably coupling the appropriate skin motion to a transducer. Any suitable conventional body-powered signal generating system may be employed. The power source may comprise a battery conveniently carried by the user, for example, a battery supported from the user's belt.

The signal output of initial stage 61 is furnished to a servo amplifier 62 through a servo preamplifier 63. Motor 53 is driven by the output of servo amplifier 62.

Servo amplifier 63 has an auxiliary output at 64 which is employed to generate an operating (lock release) signal for the elbow lock solenoid 36 at a predetermined time after motor 53 becomes energized, for example, after 2.5 seconds, considered sufficient to provide the desired amount of lifting movement of forearm portion 27 with respect to upper arm member 12. Thus, the output line 64 is connected to solenoid 36 through a 2.5-second timer 65, typically illustrated in detail in FIG. 5.

In the typical example illustrated in FIG. 5, the line 64 is connected through a 2-volt threshold detector 66 of conventional design to the input of a conventional 2.5-second one-shot 67 which generates a 2.5 second main internal pulse 68 and a b 0.1 second output pulse 69 at the end of said main pulse. The main pulse 68 is supplied through a solenoid driver stage 70 to the hook lock solenoid 60, whereby the ratchet wheel 58 is locked by pawl 59 during the 2.5 second lifting period of forearm portion 27, preventing cable 51 from opening the grasping hook assembly 47. Ratchet wheel 58 is released at the end of the 2.5 second lifting period. At the end of said 2.5 second period, the short pulse 69 is supplied through a solenoid driver stage 71 to the elbow lock solenoid 36, retracting the plunger 35 and releasing pawl member 31, causing said pawl member to move from the latched position of FIG. 3 to the elbow locking position of FIG. 2. With the elbow locked, and assuming that the shoulder joint at shaft 13 is also locked by its pawl member 14, continued energization of motor 53 will deveop sufficient tension in cable 51 to open the hoop assembly 47.

To release the forearm portion 27 it is merely necessary to unlock the elbow by means of cable 44, as above described, and allow forearm portion 27 to return to its normal depending position by gravity. The elbow will remain unlocked by the latching of pawl member 31 in its elevated position, shown in FIG. 3.

The shoulder joint pawl-releasing solenoid 21 may be operated by an independent motor-energizing and solenoid-pulsing circuit similar to that employed for the elbow joint pawl-releasing solenoid 36, using another EMG, or equivalent, signal generating site. As above mentioned, a release cable operable by the user may be employed to retract pawl member 14 to its latched lowered position to unlock the shoulder joint. As also mentioned above, with the shoulder joint unlocked, tension on cable 51 produced by motor 53 will cause upper arm member 12 to be elevated, and the upper arm member 12 will be locked after 2.5 seconds of motor action. After its elevation, the shoulder joint may also be subsequently unlocked so as to allow upper arm member 12 to return by gravity to a normal depending position.

With the shoulder joint locked and the elbow joint unlocked, tension on cable 51 causes forearm portion 27 to be elevated.

It will therefore be seen that the user can exert substantially independent control of the shoulder and elbow joints, as well as of the operation of the hook assembly 47.

Also, solenoid current drain is relatively small because of the narrowness of the solenoid release pulses (69) employed, thus prolonging battery life to an appreciable extent.

With the elements 12 and 27 in normal depending positions, the elbow joint is normally unlocked. To elevate forearm portion 27 a command signal is applied to the control input stage 61, causing motor 53 to be energized and triggering the timer 65. The forearm portion 27 is elevated to a desired position under the control of the command signal. After the 2.5 second timed period, solenoid 36 is pulsed and releases pawl member 31, causing the elbow joint to be locked in said desired position. Further actuation of motor 53 (the shoulder joint being locked) eventually causes opening of the hook assembly 47 by the tension developed in cable 51.

The sensitivity of the timer circuit 65 may be varied by suitably adjusting the threshold triggering voltage of the threshold detector 66 which senses the voltage level in the servo preamplifier 63.

The principle of the present invention may be extended to provide two-position control of wrist rotation. Such a system would use the main power cable, suitably routed, to provide 90° wrist rotation when the wrist bearing assembly is unlocked. A torsion spring may be employed to return the wrist to its original position. The locking function would be provided by an electromechanical lock arrangement similar to that above described for the elbow lock. This arrangement would allow an amputee to pre-position the wrist to either one of two positions and would add very little to the weight or complexity of the wrist joint. The present invention can be used in various environments as will now be clear to the routineer in this art, e.g. for amputees of various types, for shoulder disarticulation cases and powered elbow brace cases and in fact the present invention has been successfully tested in these environments.

Prepublished documents, relevant to the present invention, and hereby incorporated by reference, are:

1. "Development and Evaluation of Externally Powered Upper-Limb Prosthesis," Seamone et al., *Bulletin of Prosthetics Research*, Spring, 1972.

2. "Development and Evaluation of Externally Powered Upper-Limb Prosthesis," Seamone et al., *Bulletin of Prosthetics Research*, Fall, 1971.

3. "Interdisciplinary Development and Evaluation of Externally Powered Upper-Limb Prosthesis", Seamone et al., *Bulletin of Prosthetics Research*, Spring, 1973.

4. "Interdisciplinary Development of Evaluation of Externally Powered Upper-Limb Prosthesis", Seamone et al., *Bulletin of Prosthetics Research*, Fall, 1972.

While a specific embodiment of an improved prosthetic joint lock and cable system has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. In an artificial limb unit, a support adapted to be attached to the wearer's body, a limb assemblage connected to said support and including a drive motor and at least one pivoted limb member, means to energize said drive motor, cable and pulley means operatively interconnecting said limb assemblage, support and pivoted limb member for rotating said limb member responsive to energization of said drive motor, and means to lock said pivoted limb member in a rotated position at the end of a predetermined timed period following energization of said motor.

2. The artificial limb unit of claim 1, and wherein said limb assemblage comprises a first limb member pivotally connected to said support and a second limb member pivotally connected to said first limb member, said drive motor being mounted on said first limb member, and wherein said cable and pulley means includes means to rotate both of said limb members responsive to energization of said drive motor.

3. The artificial limb unit of claim 2, and wherein said second limb member is provided with a terminal device, and means operatively connecting said cable and pulley means to said terminal device.

4. The artificial limb unit of claim 2, and wherein each of said pivoted limb members is provided with means to lock it against rotation, at least one of said last-named locking means comprising said means to lock the associated limb member at the end of said predetermined timed period.

5. The artificial limb unit of claim 4, and a terminal device connected to said second limb member, and means to operate said terminal device responsive to the simultaneous locking of both of said pivoted limb members when the motor is energized.

6. The artificial limb unit of claim 1, and wherein said locking means comprises cooperating pawl and toothed wheel means on the limb assemblage and pivoted limb member, electromagnetic means controlling the cooperation of said pawl and toothed wheel means, and timer circuit means connecting said motor energizing means to said electromagnetic means.

7. The artificial limb unit of claim 6, and wherein said motor energizing means comprises transducer and control input means to generate a signal in accordance with body movement of the user, servo amplifier means drivingly connected to the motor, and means furnishing said signal to the input of the servo amplifier means.

8. The artificial limb unit of claim 7, and wherein said timer circuit means comprises delayed one-shot pulse generating means connected between said servo amplifier means and said electromagnetic means.

9. The artificial limb unit of claim 1, and wherein said support comprises a shoulder cap member and said limb assemblage comprises an upper arm member pivoted at its upper end to said shoulder cap member and a forearm portion pivoted to the lower end of said upper arm member to define an elbow joint, said cable and pulley means comprising an upper pulley supportingly connected to said shoulder cap member at a location to define a moment arm between the pulley center and the pivot axis of the upper arm member, an idler pulley journalled to said upper arm member forwardly adjacent said elbow joint, and a cable element connected to said motor extending over said upper pulley and under said idler pulley, said forearm portion being provided with a terminal device, and means operatively connecting said cable element to said terminal device.

10. The artificial limb unit of claim 9, and wherein said locking means comprises cooperating lockingly biased pawl and toothed wheel means on the upper arm member and forearm portion at said elbow joint, electromagnetic means on said upper arm member controlling the cooperation of said pawl and toothed wheel means, and timer circuit means connecting said motor energizing means to said electromagnetic means.

11. The artificial limb unit of claim 10, and wherein said electromagnetic means comprises a solenoid having a movable plunger normally extended and engageable with said pawl and toothed wheel means to hold the elbow joint unlocked, and means in the timer circuit means to pulse the solenoid and retract said plunger at the end of said predetermined time period following the energization of said motor, whereby to release said pawl and toothed wheel means for locking cooperation.

12. The artificial limb unit of claim 11, and the user-operated cable means operatively connected to said pawl and toothed wheel means to unlock same and enable said plunger to engage same to hold the elbow joint unlocked.

* * * * *